United States Patent
Nisbet et al.

(10) Patent No.: US 7,718,820 B2
(45) Date of Patent: May 18, 2010

(54) PROCESS FOR THE PREPARATION OF AN ALKANEDIOL AND A DIALKYL CARBONATE

(75) Inventors: Timothy Michael Nisbet, Amsterdam (NL); Garo Garbis Vaporciyan, Houston, TX (US); Cornelis Leonardus Maria Vrouwenvelder, Amsterdam (NL); Paul Wood, Amsterdam (NL)

(73) Assignee: Shell Oil Company, Houston, TX (US)

( * ) Notice: Subject to any disclaimer, the term of this patent is extended or adjusted under 35 U.S.C. 154(b) by 226 days.

(21) Appl. No.: 12/017,301

(22) Filed: Jan. 21, 2008

(65) Prior Publication Data

US 2008/0183002 A1 Jul. 31, 2008

(30) Foreign Application Priority Data

Jan. 23, 2007 (EP) .................. 07100967

(51) Int. Cl.
C07C 69/96 (2006.01)
(52) U.S. Cl. ...................... 558/277; 568/858
(58) Field of Classification Search .............. 558/277; 568/858
See application file for complete search history.

(56) References Cited

U.S. PATENT DOCUMENTS

| | | | | |
|---|---|---|---|---|
| 2,448,767 A | 9/1948 | Carlson | ............ | 260/284 |
| 3,803,201 A | 4/1974 | Gilpin | ............ | 260/463 |
| 4,062,884 A | 12/1977 | Romano et al. | ............ | 260/463 |
| 4,691,041 A | 9/1987 | Duranleau et al. | ............ | 558/277 |
| 5,210,268 A | 5/1993 | Fukuoka et al. | ............ | 558/270 |
| 5,344,954 A | 9/1994 | Schon et al. | ............ | 558/274 |
| 5,359,118 A | 10/1994 | Wagner et al. | ............ | 558/277 |
| 5,747,609 A | 5/1998 | Komiya et al. | ............ | 526/68 |
| 6,156,160 A | 12/2000 | Marquis et al. | ............ | 203/29 |
| 6,207,850 B1 * | 3/2001 | Jiang et al. | ............ | 558/277 |
| 6,768,020 B2 | 7/2004 | De Jonge et al. | ............ | 558/277 |
| 6,835,858 B1 | 12/2004 | De Jonge et al. | ............ | 568/716 |
| 6,953,864 B2 | 10/2005 | De Jonge et al. | ............ | 558/277 |
| 7,563,919 B2 * | 7/2009 | Van Der Heide et al. | .... | 558/277 |

FOREIGN PATENT DOCUMENTS

| | | |
|---|---|---|
| EP | 1082 | 3/1979 |
| EP | 180387 | 5/1990 |
| EP | 569812 | 11/1993 |
| EP | 274953 | 7/1998 |
| EP | 889025 | 1/1999 |
| EP | 1245608 | 5/2004 |
| EP | 1065193 | 7/2004 |
| EP | 0850972 | 6/2006 |
| JP | 0940616 | 2/1997 |
| WO | WO0003006418 | 1/2003 |
| WO | WO02005/003113 | 1/2005 |

OTHER PUBLICATIONS

Ullmann's Encyclopedia of Industrial Chemistry, 5$^{th}$ ed. vol. B4, p. 321 ff, 1992.
J F Knifton et al., J. Mol. Catal, 67 (1991) 389ff.
Hong Zhu et al., "Synthesis of Propylene Carbonate and Some Dialkyl Carbonates in the Presence of Bifunctional Catalyst Compositions," Polymers for Advanced Technologies, Wiley & Sons, Bognor Regis, GB, vol. 7, No. 8, Aug. 1, 1996, pp. 701-703 XP000623427.

* cited by examiner

Primary Examiner—Rei-tsang Shiao

(57) ABSTRACT

An alkanediol and a dialkyl carbonate are prepared in a process comprising:
(a) reacting an alkylene carbonate and an alkanol feedstock in a first reaction zone under transesterification conditions to obtain a product mixture of dialkyl carbonate, unconverted alkanol, the alkanediol, unconverted alkylene carbonate and dimers of the alkanediol;
(b) separating dialkyl carbonate and alkanol from the product mixture to obtain a bottom product stream containing alkanediol, unconverted alkylene carbonate and dimers of the alkanediol;
(c) recovering the dialkyl carbonate; and
(d) separating alkanediol from the bottom product stream to leave a recycle stream comprising unconverted alkylene carbonate and dimers of the alkanediol, which process further comprises
(e) passing at least part of the recycle stream to a second reaction zone in which the dimers of the alkanediol are converted to higher-boiling oligomers of alkanediol, yielding an oligomers-containing effluent;
(f) separating the higher-boiling oligomers from the oligomers-containing effluent yielding an alkylene carbonate-containing remaining stream; and
(g) recycling the alkylene carbonate-containing remaining stream to the first reaction zone.

18 Claims, 1 Drawing Sheet

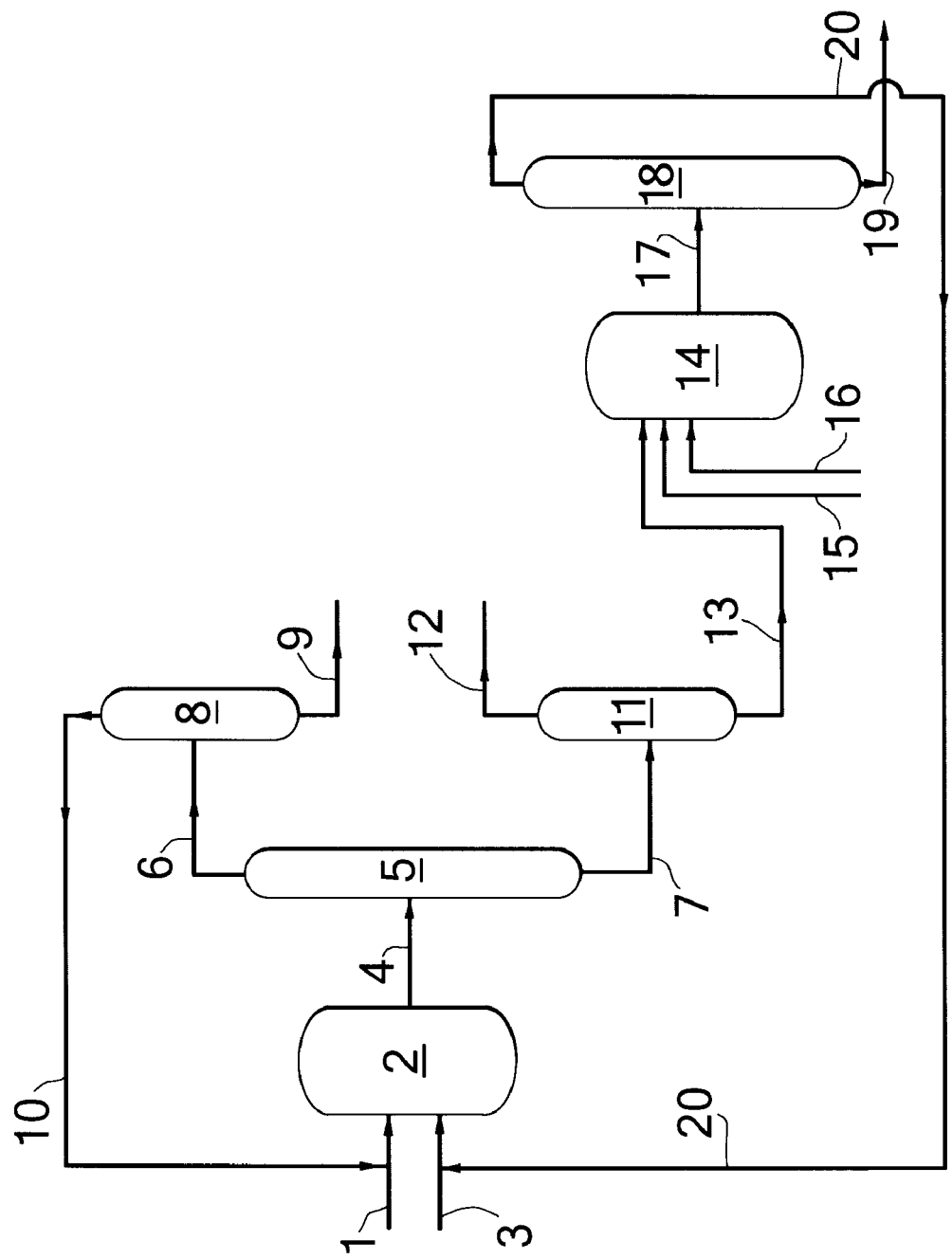

PROCESS FOR THE PREPARATION OF AN ALKANEDIOL AND A DIALKYL CARBONATE

This application claims the benefit of European Patent Application No. 07100967.4 filed on Jan. 23, 2007 that is hereby incorporated by reference.

FIELD OF THE INVENTION

The present invention relates to a process for the preparation of an alkanediol and a dialkyl carbonate. More particularly, the invention relates to a process for the preparation of such compounds from an alkylene carbonate and an alkanol.

BACKGROUND OF THE INVENTION

A process for preparing a dialkyl carbonate is described in U.S. Pat. No. 5,359,118. The patent discloses a process in which di($C_1$-$C_4$ alkyl) carbonates are prepared by transesterification of an alkylene carbonate with a $C_1$-$C_4$ alkanol. The alkylene carbonate and an alkanol feedstock are reacted countercurrently in a column with the aid of a catalyst. The catalyst is usually homogeneous, although the use of heterogeneous catalysts is also suggested. The alkylene carbonate is introduced into the upper part of the column and trickles down from above. The alkanol feedstock comprising a pure alkanol and a stream, comprising the alkanol and also the dialkyl carbonate, is fed into the column at a lower part. The alkanol flows upward and reacts countercurrently with the alkylene carbonate to obtain dialkyl carbonate with unreacted alkanol as the top effluent and the alkanediol with any entrained alkanol as the bottom effluent. The top effluent is subjected to distillation treatments to yield an alkanol-rich stream comprising the alkanol and minor amounts of the dialkyl carbonate. This stream is fed to the column as part of the alkanol feedstock. The bottom stream is worked-up resulting in an alkylene glycol stream and a catalyst-containing concentrate that is partly recycled.

The patent discloses the formation of high-boiling by-products, such as polyglycols. In the process these high-boiling by-products are contained in the catalyst-containing concentrate. Part of the concentrate is recycled to the transesterification, whereas another part is discarded.

Although the process discloses the formation of polyglycols, it does not address the problem of the removal of such polyglycols, in particular the dimers of the alkanediol, also known as dialkylene glycols. Moreover, the process presumes that no alkylene carbonate leaves the reactor unconverted. In practice, the transesterification to dialkyl carbonate will not be 100%. Therefore, the bottom product of the process will contain not only polyglycols, as suggested in U.S. Pat. No. 5,359,118, but also some unconverted alkylene carbonate. In view of their boiling points it is very difficult to separate dialkylene glycols from the corresponding alkylene carbonates. This has not been acknowledged in the process according to U.S. Pat. No. 5,359,118. Therefore the bottom product contains contaminants that bear the risk of building up during continuous recycle.

It is an object of the present invention to overcome this drawback.

SUMMARY OF THE INVENTION

The present invention provides a process for the preparation of an alkanediol and a dialkyl carbonate comprising:

(a) reacting an alkylene carbonate and an alkanol feedstock in a first reaction zone under transesterification conditions to obtain a product mixture of dialkyl carbonate, unconverted alkanol, the alkanediol, unconverted alkylene carbonate and dimers of the alkanediol;

(b) separating dialkyl carbonate and alkanol from the product mixture to obtain a bottom product stream containing alkanediol, unconverted alkylene carbonate and dimers of the alkanediol;

(c) recovering the dialkyl carbonate; and (d) separating alkanediol from the bottom product stream to leave a recycle stream comprising unconverted alkylene carbonate and dimers of the alkanediol, which process further comprises (e) passing at least part of the recycle stream to a second reaction zone in which dimers of the alkanediol are converted to higher-boiling oligomers of alkanediol, yielding an oligomers-containing effluent;

(f) separating the higher-boiling oligomers from the oligomers-containing effluent yielding an alkylene carbonate-containing remaining stream; and (g) recycling the alkylene carbonate-containing remaining stream to the first reaction zone.

The present invention is based on the finding that the separation of higher-boiling by-products from alkylene carbonates can be rendered easy by converting dialkylene glycols to higher-boiling oligomers of alkanediol. By the subsequent easy separation the build-up of dialkylene glycols is prevented. By the recycle of the remaining alkylene carbonate, this part of the alkylene carbonate in the recycle stream is subjected to the transesterification again, so that it may be converted into the target dialkyl carbonate.

BRIEF DESCRIPTION OF THE DRAWINGS

FIG. 1 depicts a flow scheme for the process according to the present invention.

DETAILED DESCRIPTION OF THE INVENTION

The present invention provides a process for the preparation of an alkanediol and a dialkyl carbonate. The reaction zone in the present invention may be a reactive distillation zone, as described in U.S. Pat. No. 5,359,118. This would entail that the reaction is carried out counter-currently. The transesterification reaction is advantageously conducted in a column furnished with internals, like a distillation column. Hence, it may contain trays with bubble caps, sieve trays, or Raschig rings. The skilled person will realise that several packing types and tray configurations will be possible. Suitable columns have been described in, e.g., Ullmann's Encyclopedia of Industrial Chemistry, $5^{th}$ ed. Vol. B4, pp 321 ff, 1992. The alkylene carbonate will be fed at the upper part of such a column and will flow down. The alkylene carbonate will generally have a higher boiling point than the alkanol. In the case of ethylene and propylene carbonate the atmospheric boiling points are above 240° C. The alkylene carbonate will flow down over the trays or rings and be brought into contact with the alkanol that flows upward.

In a preferred embodiment the reaction is conducted in a co-current manner. A suitable way to operate is to carry out the reaction in a trickle-flow manner wherein the reactants, part in vapor phase and part in liquid phase, drip down over a heterogeneous catalyst. A more preferred way to operate the process of the present invention is in a reactor with only liquids. A suitable reaction zone of this type is a pipe-type reaction zone wherein the reaction is conducted in a plug flow manner. This will enable the reaction to run to virtual completion. A further possibility is to conduct the reaction in a continuously stirred tank reactor (CSTR). In the latter case the effluent from the CSTR is preferably subjected to a post-reaction in a plug flow reactor so that the reaction runs to virtual completion.

The process of the present invention includes the transesterification of an alkylene carbonate with an alkanol. This transesterification reaction is described in U.S. Pat. No. 5,359,118. The starting materials of the transesterification are preferably selected from $C_2$-$C_6$ alkylene carbonate and $C_1$-$C_4$ alkanols. More preferably the starting materials are ethylene carbonate or propylene carbonate and methanol, ethanol or isopropanol.

Transesterification conditions suitably include the presence of a catalyst. Suitable homogeneous catalysts have been described in U.S. Pat. No. 5,359,118 and include hydrides, oxides, hydroxides, alcoholates, amides, or salts of alkali metals, i.e., lithium, sodium, potassium, rubidium and cesium. Preferred catalysts are hydroxides or alcoholates of potassium or sodium. It is advantageous to use the alcoholate of the alkanol that is being used as feedstock. Such alcoholate can be added as such or be formed in situ.

Other suitable catalysts are alkali metal salts, such as acetates, propionates, butyrates, or carbonates. Further suitable catalysts are described in U.S. Pat. No. 5,359,118 and the references mentioned therein, such as EP 274 953, U.S. Pat. No. 3,803,201, EP 1082, and EP 180 387.

As indicated in U.S. Pat. No. 5,359,118, it is also possible to employ heterogeneous catalysts. In the current process the use of heterogeneous catalysts in the transesterification reaction is preferred. Suitable heterogeneous catalysts include ion exchange resins that contain functional groups. Suitable functional groups include tertiary amine groups and quaternary ammonium groups, and also sulfonic acid and carboxylic acid groups. Further suitable catalysts include alkali and alkaline earth silicates. Suitable catalysts have been disclosed in U.S. Pat. No. 4,062,884 and U.S. Pat. No. 4,691,041. Preferably, the heterogeneous catalyst is selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff.

The transesterification conditions are known to one of ordinary skill in the art and suitably include a temperature from 40 to 200° C., and a pressure from 50 to 5000 kPa (0.5 to 50 bar). When the alkanol is methanol, the pressure is preferably close to atmospheric. The temperature depends on the alkanol feedstock and pressure used, and the reactor used. In counter-current mode the temperature is kept such that it is close to and above the boiling point of the alkanol, e.g. up to 5° C. above the boiling point. In the case of methanol and atmospheric pressure, the temperature is close to and above 65° C., for instance between 65 and 70° C. In case of co-current operation the alkanol may still be liquid. In co-current operation, the pressure ranges suitably from 0.5 to 50 bar, preferably from 2 to 20 bar, and the temperature from 40 to 200° C., preferably from 80 to 160° C.

When the transesterification catalyst is homogeneous such as an alkali metal alcoholate, and when a reactive distillation is being employed, the homogeneous catalyst, may be introduced in the upper part of the reaction zone. The alkanol feedstock is then introduced at a lower point. The feedstock may be completely in vapour phase. However, it is also possible to introduce the feedstock into the column partly in the liquid phase. It is believed that the liquid phase ensures a higher concentration of alkanol in the lower part of the column with a beneficial effect on the overall transesterification. It is distributed over the width of the column via the inlet and the column internals. The ratio between the vapor and the liquid part of the alkanol feedstock may be varied between wide ranges. The vapor/liquid weight ratio is suitably from 1:1 to 10:1 wt/wt.

When a heterogeneous catalyst bed is being used and when a reactive distillation is being employed, the alkylene carbonate is suitably introduced above the catalyst bed and the alkanol below the catalyst bed. When a co-currently operated reactor is being employed the reactants may be pre-mixed or introduced separately into the reactor upstream of the catalyst bed. The person skilled in the art will know that the transesterification is an equilibrium reaction. Therefore, the process may suitably employ an excess of the alkanol. The molar ratio of alkanol to alkylene carbonate is suitably from 1.01:1 to 25:1, preferably from 2:1 to 15:1, more preferably from 3:1 to 7:1. The amount of catalyst can evidently be much smaller. In case of the use of a homogeneous catalyst suitable amounts of such catalysts include from 0.1 to 5.0% wt based on alkylene carbonate, preferably from 0.2 to 2% wt. The weight hourly space velocity may suitably range from 0.1 to 100 kg/kg·hr.

From the reaction zone a mixture of dialkyl carbonate, unconverted alkanol, alkanediol, unconverted alkylene carbonate and dimer of alkanediol is withdrawn. In the case of a counter-current process, such as reactive distillation, a first mixture of alkanol and dialkyl carbonate is withdrawn at the top of the reactive distillation column, and at the bottom a second mixture comprising unconverted alkylene carbonate, alkanediol and dimer of alkanediol. In case of a co-current operation a product mixture comprising the above-mentioned five compounds is obtained.

When the transesterification is being conducted in a reactive distillation unconverted alkanol and dialkyl carbonate are separated together in the reactive distillation zone and withdrawn at the upper part of a reactive distillation column. Unconverted alkylene carbonate and alkanediol are withdrawn from the reactive distillation column at the lower part. In other embodiments the four compounds are withdrawn simultaneously. In one embodiment the unconverted alkanol and the dialkyl carbonate are separated by distillation in one fraction. Suitable distillation conditions are a pressure from 0.1 to 1.0 bar and a temperature from 40 to 200° C. This achieves the separation of a top fraction comprising unconverted alkanol and dialkyl carbonate and a bottom fraction comprising unconverted alkylene carbonate and alkanediol. The top fraction is preferably subjected to another distillation to separate dialkyl carbonate from unconverted alkanol. Such distillation may suitably be achieved at pressures ranging from subatmospheric pressure to superatmospheric pressure. Suitably the pressure may vary from 0.1 to 45 bar. Temperatures may vary in accordance with the pressure selected. The temperature may be from 35 to 300° C. More preferably, the conditions in the distillation include a pressure ranging from 0.1 to 0.5 bar and a temperature ranging from 35 to 150° C. When the dialkyl carbonate and the alkanol form an azeotrope it may be beneficial to use extractive distillation, using an extractant to facilitate the separation between the dialkyl carbonate and the alkanol. The extractant can be selected from many compounds, in particular alcohols such as phenol, or anisole. However, it is preferred to employ an alkylene carbonate as extractant. It is most advantageous to obtain the separation in the presence of the alkylene carbonate that is being used as starting material for the eventual alkanediol.

In another embodiment the product stream is subjected to distillation in such a manner that mainly unconverted alkanol is separated as top fraction. Such a distillation may suitably be carried out at a pressure of 0.1 to 45 bar. Temperatures may vary in accordance with the pressure selected. The temperature may be from 35 to 300° C. More preferably, the pressure is from 0.5 to 1.5 bar and the temperature ranges from 60 to 200° C. In a further distillation the remaining compounds may be separated in dialkyl carbonate as top fraction and a bottom fraction comprising alkanediol and unconverted alkylene carbonate. Conditions for this distillation advantageously include a pressure of 0.1 to 0.5 bar and a temperature of 60 to 190° C.

The dialkyl carbonate recovered in the embodiments may optionally be further purified. This further purification may comprise a further distillation step or an ion-exchange step, as described in U.S. Pat. No. 5,455,368.

Both in the counter-current and the co-current embodiments a bottom product is obtained comprising alkanediol, unconverted alkylene carbonate and dialkylene glycol. To separate alkanediol from this bottom stream the bottom stream is preferably subjected to a further distillation step, suitably at a pressure from 0.01 to 0.4 bar and a temperature of 100 to 200° C. This distillation achieves a separation of alkanediol and a recycle stream comprising unconverted alkylene carbonate. The top fraction in this distillation containing recovered alkanediol may comprise other compounds, such as unconverted alkylene carbonate depending on the sharpness of the separation cut.

At least a part of the recycle stream is passed to the second reaction zone. Suitably the complete recycle stream is fed to the second reaction zone. Optionally, the stream may be split in more portions, the additional portions being bled from the process. It will be understood that in general the bleed stream will be as small as feasible, and preferably, no bleed stream will be used in the process In the second reaction zone the dimer of the alkanediol is converted to higher-boiling oligomers of the alkanediol. Suitably this is effected by the reaction of the dimer with an alkylene oxide or an alkylene carbonate. When an alkylene carbonate is being used, the reaction conditions and catalyst may be selected from those that are being used in the first reaction zone. The condition for the reaction of alkylene carbonate with alcohols are well known and have been described in U.S. Pat. No. 2,448,767. It is possible to employ the same alkylene carbonate that is being used in the first reaction zone. In such a case the alkylene carbonate that is present in the recycle stream comprising unconverted alkylene carbonate and dimers of the alkanediol may be employed for this reaction. Depending on the content of the dimer of the alkanediol and of the alkylene carbonate in this recycle stream additional alkylene carbonate may be added.

Suitably the molar ratio of alkylene carbonate or alkylene oxide to dimer of alkanediol is at least 1:1. Molar ratios can be much higher and there is usually no upper limit. Since the dimer formation is limited and the reaction of dimer with alkylene carbonate is fast there is usually an excess of alkylene carbonate. An excess ratio of more than 1000:1 is not common.

Preferably, the higher-boiling oligomers of alkanediol are prepared by adding an alkylene oxide to the second reaction zone. In this method it is easy to optimise the molar ratio between the reactants. Further the reaction between the dimer and alkylene oxide is fast and runs easily to completion.

The alkylene oxide in this embodiment contains preferably the same alkylene moiety as the one in the alkylene carbonate. In this way oligomers of the same alkanediol are obtained that may be recovered as useful products.

The reaction conditions for the reaction of the dimer of alkanediol with an alkylene oxide are known in the art. Reaction conditions include a reaction temperature in the range of 70 to 250° C., preferably from 90 to 180° C., a pressure in the range of 0.5 to 15 bar, preferably from 1 to 6 bar. The reaction is preferably conducted in the presence of an alkali catalyst. Suitable catalysts include alkali metal hydroxides, in particular sodium and potassium hydroxide. The catalyst is preferably added in an amount of 0.01 to 5% wt, based on the amount of the dimer, more preferably in an amount of 0.1 to 1% wt, based on the weight of the dimer.

The reaction rate of the oligomer formation is high and the reaction is bound to run to virtual completion. However, the objective of the present invention, i.e. the prevention of the build-up of the dimer of the alkanediol, is achieved, even if the reaction is not complete. This will provide the skilled artisan with freedom to select the most feasible conditions.

After the formation of the oligomers the resulting oligomers-containing effluent is subjected to separation. Suitably the effluent is subjected to distillation. In such distillation the alkylene carbonate present in the effluent can be withdrawn from the upper part of the distillation column as the alkylene carbonate-containing remaining stream, whereas the oligomers together with the alkaline catalyst can be withdrawn at the lower part of the column. The oligomers and catalyst may be discharged or treated to recover the oligomer as useful product and/or recover the alkaline catalyst for re-use. Distillation conditions may be selected by the skilled person. Suitably, the distillation is conducted under vacuum. The pressure is preferably from 10 mbar to 1 bar. The temperature in the distillation may suitably range from 100 to 300° C.

Since the alkylene carbonate-containing remaining stream is recycled to the first reaction zone no alkylene carbonate is wasted and all starting material is converted to the desired products.

The process of the present invention can be employed for a variety of feedstocks. The process is excellently suited for the preparation of ethylene glycol (1,2-ethanediol), propylene glycol (1,2-propanediol), dimethyl carbonate and/or diethyl carbonate and/or diisopropyl carbonate. The process is most advantageously used for the production of ethylene glycol or propylene glycol and diethyl carbonate or diisopropyl carbonate from ethylene carbonate or propylene carbonate and ethanol or isopropanol. The dimer of the alkanediol is suitably converted to the trimer. In this way the separation becomes easy and the addition of extra starting material such as alkylene oxide can be kept minimal. Therefore, the oligomers to be produced are most preferably triethylene glycol and tripropylene glycol.

In FIG. 1, a flow scheme for the process according to the present invention is shown. Although the process will be described for ethanol as a suitable alcohol and ethylene carbonate as the alkylene carbonate the skilled person will understand that other alkanols and alkylene carbonates can be similarly used.

Ethanol is passed via line 1 into reactor 2. Reactor 2 can suitably be a continuously stirred tank reactor. Via line 3 ethylene carbonate is also fed into reactor 2. A transesterification catalyst may be present or may be fed continuously to the reactor. The catalyst may be mixed with one of the reactants or fed to the reactor via a separate line (not shown). A product comprising a mixture of diethyl carbonate, unconverted ethanol, ethylene glycol and unconverted ethylene carbonate is withdrawn from the reactor 2 via line 4. Via line 4 the mixture is passed to a distillation column 5 where the product is separated into a top fraction comprising diethyl carbonate and ethanol that is withdrawn via line 6, and a bottom fraction comprising ethylene glycol and ethylene carbonate withdrawn via line 7. The mixture comprising diethyl carbonate and ethanol in line 6 is passed to a distillation column 8, where the mixture is separated into ethanol and diethyl carbonate. The diethyl carbonate is discharged via line 9 and recovered as product, optionally after further purification. Ethanol is recovered via line 10 and recycled to reactor 2 via line 1.

The bottom stream in line 7 is subjected to distillation in distillation column 11. In the distillation column 11 a top product comprising ethylene glycol is recovered via line 12. Since the top product may be slightly contaminated with some ethylene carbonate further purification may be considered. The bottom product of distillation column 11 withdrawn via line 13 comprises polyethylene glycol, in particular diethylene glycol, and ethylene carbonate. Through line 13 the bottom product is passed to reactor 14, into which also ethylene oxide is passed via line 15, and homogeneous catalyst via line 16. Reactor 14 is shown as a continuously stirred tank reactor. However, other reactors, such as pipe reactors with a plug flow regime, are also possible. The reaction product from reactor 14 is withdrawn via line 17 and passed to distillation column 18. In distillation column 18 a bottom product is withdrawn via line 19, comprising the oligomers of ethylene glycol, in particular triethylene glycol. The top fraction of distillation column 18, withdrawn via line 20, comprises ethylene carbonate and is recycled to reactor 2.

What is claimed is:

1. A process for the preparation of an alkanediol and a dialkyl carbonate comprising:
   (a) reacting an alkylene carbonate and an alkanol feedstock in a first reaction zone under transesterification conditions to obtain a product mixture of dialkyl carbonate, unconverted alkanol, the alkanediol, unconverted alkylene carbonate and dimers of the alkanediol;
   (b) separating dialkyl carbonate and alkanol from the product mixture to obtain a bottom product stream containing alkanediol, unconverted alkylene carbonate and dimers of the alkanediol;
   (c) recovering the dialkyl carbonate; and
   (d) separating alkanediol from the bottom product stream to leave a recycle stream comprising unconverted alkylene carbonate and dimers of the alkanediol, which process further comprises
   (e) passing at least part of the recycle stream to a second reaction zone in which the dimers of the alkanediol are converted to higher-boiling oligomers of alkanediol, yielding an oligomers-containing effluent;
   (f) separating the higher-boiling oligomers from the oligomers-containing effluent yielding an alkylene carbonate-containing remaining stream; and
   (g) recycling the alkylene carbonate-containing remaining stream to the first reaction zone.

2. A process as claimed in claim 1, wherein the reaction in the first reaction zone is conducted in a co-current manner.

3. A process as claimed in claim 2, wherein the reaction is conducted in a plug flow manner.

4. A process as claimed in claim 1, wherein a heterogeneous catalyst is used in the transesterification reaction.

5. A process as claimed in claim 1, wherein the temperature in the first reaction zone is from 40 to 200° C., and the pressure from 0.5 to 50 bar.

6. A process as claimed in claim 1, wherein unconverted alkanol and the dialkyl carbonate are separated by distillation in one fraction.

7. A process as claimed in claim 1, wherein the bottom product stream is subjected to a further distillation to achieve a separation of alkanediol and a recycle stream comprising unconverted alkylene carbonate and dimers of alkanediol.

8. A process as claimed in claim 7, wherein the separated alkanediol is obtained in a stream further comprising unconverted alkylene carbonate.

9. A process as claimed in claim 1, wherein the dimers of alkanediol are converted to higher-boiling oligomers of alkanediol with an alkylene carbonate.

10. A process as claimed in claim 9, wherein the dimers of the alkanediol are converted under transesterification conditions as in the first reaction zone.

11. A process as claimed in claim 9, wherein the dimers of alkanediol are converted to higher-boiling oligomers of alkanediol with an alkylene oxide.

12. A process as claimed in claim 11, wherein the dimers are converted in the presence of an alkaline catalyst.

13. A process as claimed in claim 11, wherein the reaction conditions in the second reaction zone include a pressure ranging from 0.5 to 15 bar and a temperature ranging from 70 to 250° C.

14. A process as claimed in claim 11, wherein the reaction conditions in the second reaction zone include a pressure ranging from 1 to 6 bar, and a temperature ranging from 90 to 180° C.

15. A process as claimed in claim 9, wherein the molar ratio between and alkylene carbonate or alkylene oxide and the dimer of alkanediol ranges from 1:1 to 1000:1.

16. A process as claimed in claim 1, wherein the alkylene carbonate is selected from the group consisting of ethylene carbonate and propylene carbonate.

17. A process as claimed in claim 1, wherein the alkanol is selected from the group consisting of ethanol and isopropanol.

18. A process as claimed in claim 1, wherein the oligomer is selected from the group consisting of triethylene glycol and tripropylene glycol.

* * * * *